United States Patent
Junger et al.

(10) Patent No.: US 11,389,239 B2
(45) Date of Patent: Jul. 19, 2022

(54) ENHANCED FIBER PROBES FOR ELT

(71) Applicant: ELIOS VISION, INC., Los Angeles, CA (US)

(72) Inventors: Johannes Junger, Gilching (DE); Markus Enders, Munich (DE)

(73) Assignee: ELIOS VISION, INC., Los Angeles, CA (US)

( * ) Notice: Subject to any disclaimer, the term of this patent is extended or adjusted under 35 U.S.C. 154(b) by 0 days.

(21) Appl. No.: 16/389,386

(22) Filed: Apr. 19, 2019

(65) Prior Publication Data

US 2020/0330157 A1    Oct. 22, 2020

(51) Int. Cl.
*A61F 9/08* (2006.01)
*A61B 18/22* (2006.01)
(Continued)

(52) U.S. Cl.
CPC .......... *A61B 18/22* (2013.01); *A61F 9/00781* (2013.01); *A61F 9/00802* (2013.01);
(Continued)

(58) Field of Classification Search
CPC .......... A61B 18/22; A61B 2017/00057; A61B 2018/00321; A61F 9/00781;
(Continued)

(56) References Cited

U.S. PATENT DOCUMENTS

| | | |
|---|---|---|
| 4,607,622 A | 8/1986 | Fritch et al. |
| 4,862,888 A * | 9/1989 | Yessik .................... A61F 9/008 606/4 |

(Continued)

FOREIGN PATENT DOCUMENTS

| | | |
|---|---|---|
| DE | 19920615 A1 | 12/2000 |
| DE | 10023176 A1 | 11/2001 |

(Continued)

OTHER PUBLICATIONS

Crandall, Alan, "Combining Cataract and Glaucoma Surgery", Review of Ophthalmology, 1-4, Jun. 13, 2008.

(Continued)

*Primary Examiner* — Ankit D Tejani
*Assistant Examiner* — Joshua Brendon Solomon
(74) *Attorney, Agent, or Firm* — Greenberg Traurig, LLP; David J. Dykeman; Roman Fayerberg

(57) ABSTRACT

Systems for treatment of glaucoma comprise an excimer laser, a plurality of fiber probes, and a processor. Each fiber probe is attachable to the excimer laser to treat a subject having glaucoma by delivering shots from the laser. The processor is configured to monitor and limit a variable number of shots delivered by each fiber probe, the number of shots delivered by each fiber probe programmable within a range. Methods of treating glaucoma include programming a fiber probe to deliver a number of shots from an excimer laser. The fiber probe is inserted into an eye of a subject having glaucoma and adjusted to a position transverse to Schlemm's canal in the eye. A plurality of shots is applied from the excimer laser source while the probe is in the transverse position, thereby treating glaucoma by creating a plurality of perforations in Schlemm's canal and/or the trabecular meshwork.

20 Claims, 9 Drawing Sheets

(51) Int. Cl.
  *A61F 9/008* (2006.01)
  *A61F 9/007* (2006.01)
  *A61B 18/00* (2006.01)
  *A61F 9/00* (2006.01)
  *A61B 17/00* (2006.01)

(52) U.S. Cl.
  CPC .............. *A61B 2017/00057* (2013.01); *A61B 2018/00321* (2013.01); *A61F 9/0017* (2013.01); *A61F 2009/00844* (2013.01); *A61F 2009/00891* (2013.01)

(58) Field of Classification Search
  CPC ................ A61F 9/00802; A61F 9/0017; A61F 2009/00844; A61F 2009/00891
  See application file for complete search history.

(56) References Cited

U.S. PATENT DOCUMENTS

| | | |
|---|---|---|
| 5,323,766 A | 6/1994 | Uram |
| 5,738,677 A | 4/1998 | Colvard et al. |
| 6,197,056 B1 | 3/2001 | Schachar |
| 6,283,974 B1 | 9/2001 | Alexander |
| 6,743,221 B1 | 6/2004 | Hobart et al. |
| 11,076,933 B2 | 8/2021 | Junger et al. |
| 11,076,992 B2 | 8/2021 | Junger et al. |
| 11,103,382 B2 | 8/2021 | Junger et al. |
| 2002/0013572 A1 | 1/2002 | Berlin |
| 2004/0082939 A1 | 4/2004 | Berlin |
| 2005/0192480 A1 | 9/2005 | Toriya et al. |
| 2006/0244652 A1 | 11/2006 | Tethrake et al. |
| 2007/0122096 A1 | 5/2007 | Temelkuran et al. |
| 2007/0147752 A1 | 6/2007 | Weisberg et al. |
| 2007/0219601 A1 | 9/2007 | Neuberger |
| 2007/0265602 A1 | 11/2007 | Mordaunt et al. |
| 2008/0054073 A1 | 3/2008 | Charles |
| 2008/0082078 A1* | 4/2008 | Berlin ................ A61F 9/00802 604/521 |
| 2008/0097415 A1 | 4/2008 | Zimare et al. |
| 2008/0108981 A1 | 5/2008 | Telfair et al. |
| 2008/0108983 A1 | 5/2008 | Nadolski |
| 2008/0161781 A1 | 7/2008 | McArdle et al. |
| 2009/0118715 A1 | 5/2009 | Mansour |
| 2009/0157064 A1 | 6/2009 | Hodel |
| 2010/0019125 A1 | 1/2010 | Stefani et al. |
| 2010/0068141 A1 | 3/2010 | Kaushal et al. |
| 2010/0324543 A1 | 12/2010 | Kurtz et al. |
| 2011/0295243 A1 | 12/2011 | Peyman |
| 2012/0275481 A1 | 11/2012 | Riggs |
| 2013/0041357 A1* | 2/2013 | Neuberger ............. A61N 5/062 606/15 |
| 2013/0085484 A1 | 4/2013 | Van Valen et al. |
| 2014/0058367 A1 | 2/2014 | Dantus |
| 2014/0188096 A1 | 7/2014 | Chia et al. |
| 2014/0316388 A1 | 10/2014 | Hipsley |
| 2015/0148615 A1 | 5/2015 | Brennan et al. |
| 2015/0217133 A1* | 8/2015 | Angeley ............... A61K 48/005 607/91 |
| 2015/0297408 A1 | 10/2015 | Dolzan et al. |
| 2015/0305811 A1* | 10/2015 | Neuberger ........... A61N 5/0616 606/11 |
| 2015/0374549 A1 | 12/2015 | Scott |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1 | 9/2018 | Aljuri et al. |
| 2018/0303667 A1* | 10/2018 | Peyman ................ A61B 34/35 |
| 2018/0353328 A1 | 12/2018 | Bacher et al. |
| 2018/0360310 A1* | 12/2018 | Berlin .................... A61F 9/008 |
| 2019/0105200 A1 | 4/2019 | Hipsley |
| 2019/0262071 A1 | 8/2019 | Thom et al. |
| 2020/0330181 A1 | 10/2020 | Junger et al. |
| 2020/0330266 A1 | 10/2020 | Junger et al. |
| 2020/0330274 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |

FOREIGN PATENT DOCUMENTS

| | | |
|---|---|---|
| EP | 1835862 B1 | 6/2011 |
| WO | 2020215062 A1 | 10/2020 |
| WO | 2020215064 A1 | 10/2020 |
| WO | 2020215066 A1 | 10/2020 |
| WO | 2020215067 A1 | 10/2020 |
| WO | 2020215068 A1 | 10/2020 |
| WO | 2020215069 A1 | 10/2020 |
| WO | 2020215071 A1 | 10/2020 |

OTHER PUBLICATIONS

Grover, Davinder S. "When You Have Cataracts and Glaucoma", Glaucoma Research Foundation, Oct. 29, 2017.

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

International Search Report in International Application No. PCT/US2020/028977 dated Sep. 23, 2020.

U.S. Appl. No. 16/389,404 US20200330275A1, filed Apr. 19, 2019 Oct. 22, 2020, Combination Treatment Using Phaco and ELT.

U.S. Appl. No. 16/389,437 US20200330281A1, filed Apr. 19, 2019 Oct. 22, 2020, Excimer Laser Fiber Illumination.

U.S. Appl. No. 16/389,346 US20200330181A1, filed Apr. 19, 2019 Oct. 22, 2020, Authentication Systems and Methods for an Excimer Laser System.

U.S. Appl. No. 16/389,359 US20200330279A1, filed Apr. 19, 2019 Oct. 22, 2020, Calibration System for Improving Manufacture Tolerance in Excimer Laser Optical Fibers.

U.S. Appl. No. 16/389,446 US20200330266A1, filed Apr. 19, 2019 Oct. 22, 2020, Combination Treatment Using ELT.

U.S. Appl. No. 16/389,460 US20200330274A1, filed Apr. 19, 2019 Oct. 22, 2020, Methods of Transverse Placement in ELT.

U.S. Appl. No. 16/389,425 US20200330280A1, filed Apr. 19, 2019 Oct. 22, 2020, Personalization of Excimer Laser Fibers.

Leung et al. "Anterior Chamber Angle Measurement with Anterior Segment Optical Coherence Tomography: A Comparison between Slit Lamp OCT and Visante OCT" IOVS, Aug. 2008, 3469-3474 (Year: 2008).

* cited by examiner

ENHANCED FIBER PROBES FOR ELT

TECHNICAL FIELD

The invention relates generally to excimer laser trabeculostomy (ELT) and fiber probes used in ELT procedures.

BACKGROUND

Patients suffering from glaucoma experience vision loss from a build-up of fluid in the anterior chamber of the eye. The fluid build-up increases the pressure in the eye and causes damage to the optic nerve. If left untreated, the damage to the optic nerve will lead to blindness.

Traditional pharmaceuticals prescribed to treat glaucoma do not provide a permanent solution and instead manage the condition by lowering pressure in the eye. For example, some medications decrease production of the fluid, while other medications increase drainage of the fluid. Traditional surgical treatments are also used to lower pressure, for example, by inserting an implant into the eye to increase drainage. However, these procedures have risks associated with them, such as dislodgement of the implant.

SUMMARY

The invention provides systems and methods of treating glaucoma using fiber probes that have a programmable number of laser shots for use during an excimer laser trabeculostomy (ELT) procedure. ELT is a minimally invasive method of treating glaucoma that does not involve implants. Instead, an excimer laser is used to permanently perforate the drainage system in the eye to increase drainage of fluid. ELT instruments require fiber probes to deliver the laser pulse to the eye. In the invention, a fiber probe connected to the ELT instrument is programmable to deliver a variable number of laser shots and monitor the number of shots delivered by the probe, thereby allowing for personalized treatment of glaucoma.

Existing fiber probes are operable for a fixed number of laser shots. Typically, a maximum number of laser shots is delivered by each existing fixed-use fiber probe. If a physician requires greater than 10 laser shots for treatment, the ELT procedure is interrupted in order to change out one fixed-use fiber probe for another fixed-use fiber probe.

Because ELT procedures often require more than a standard number of laser shots for treatment of glaucoma, the invention provides fiber probes programmable to increase the maximum number of laser shots for each probe. By programming the fiber probes, interruptions in the ELT procedure are avoided, such as delays caused by replacing an expended fixed-use fiber probe with a fresh fixed-use fiber probe in order to continue treatment of an eye. The invention therefore avoids interruptions to the surgical process in order to allow a change of equipment.

Methods and systems of the invention allow programming of a fiber probe to deliver a variable number of laser shots and monitor the number of shots delivered by the probe. In an embodiment of the invention, once the fiber probe is connected to the ELT instrument, the fiber probe may be programmed. The ELT instrument comprises an interactive user interface, or display panel, that is communicatively coupled with a controller and a processor. Settings input by the user into the interactive user interface are processed and implemented.

In an example of the invention, a physician uses the interactive user interface to enter a numerical value for the variable number of laser shots deliverable by the probe. The numerical value for the variable number of laser shots is programmable within a range and is adjustable from a minimum amount to a maximum amount. For safety purposes, the manufacturer may set a predefined limit on the maximum number of shots. The physician may program the variable number of deliverable laser shots up to the manufacturer-set maximum number. The ELT instrument programs the variable number of laser shots deliverable by the fiber probe and subsequently monitors the number of laser shots delivered by the fiber probe. The invention therefore provides personalized glaucoma treatment, which has the benefit of preventing reuse of medical equipment and avoids the detriment of not treating a patient in an optimal manner.

In some examples, the variable number of deliverable laser shots is determined based on pre-operative analysis conducted by the physician. For example, a physician may review the condition of glaucoma in the subject and decide to administer 15 laser shots per eye using ELT treatment. The physician is then able to program the fiber probe accordingly and perform the ELT procedure to deliver as many laser shots as programmed without interrupting the treatment to change out fiber probes. Thus, methods and systems of the invention provide personalized laser surgical intervention that increases efficiency of ELT procedures and avoids delays from changing out fiber probes.

During the ELT procedure of the invention, after programming the fiber probe, the physician guides the delivery tip of the fiber probe through a corneal incision in the eye and towards the trabecular meshwork. In some examples, methods of the invention further comprise administering anesthesia to the subject before making the incision and inserting the probe. Typically, the incision has a length of about ⅛ inch or smaller. In some examples of the invention, one or more sutures are used to close the incision after ELT treatment. The delivery tip is guided by the physician to a position transverse to the Schlemm's canal to create permanent perforations in the trabecular meshwork and/or Schlemm's canal. Fluid drainage from the anterior chamber of the eye is immediately improved once perforations are created in the meshwork and/or Schlemm's canal by the laser. The perforations also increase blood flow and reduce pressure in the eye. In some cases, the physician uses a Gonio lens, endoscope, or other illumination source to aid in positioning the delivery tip of the fiber probe.

Once the delivery tip is at a position transverse to the Schlemm's canal, a series of shots of laser energy are delivered to the trabecular meshwork. By providing a laser probe at a position transverse to Schlemm's canal, or crosswise to Schlemm's canal, energy from the laser is delivered to a greater amount of surface area than if the fiber probe was in a position parallel to or perpendicular to Schlemm's canal. Arrangement of the delivery tip at a position transverse to Schlemm's canal achieves optimal photoablation and formation of perforations for drainage.

To improve drainage of the aqueous humor from the anterior chamber of the eye, a plurality of permanent perforations is lasered into the trabecular meshwork and/or Schlemm's canal by the ELT procedure. Each ELT perforation has a diameter of about 200 μm. In existing fiber probes for use in ELT procedures, the fiber probes are set to deliver a maximum, fixed number of laser shots. For example, the maximum, fixed number may be 10 laser shots. Methods and systems of the present invention allow the physician to program the number of laser shots deliverable by the fiber probes, thereby providing fiber probes with a variable number of deliverable laser shots. The number of laser shots is programmable within a range and is adjustable from a minimum amount to a maximum amount. According to the invention, a physician can attach a fiber probe to the ELT instrument and enter a range for number of shots deliverable by the attached fiber probe using the interactive user interface on the instrument. In some examples of the invention, the number of deliverable laser shots is a variable number. In some examples, the variable number of deliverable shots is greater than about 10 shots.

In an example of the invention, after examining a subject having glaucoma, a physician determines that 15 shots per eye are needed for treatment. Using the invention, the physician programs a fiber probe to deliver 15 laser shots as a maximum number in the range of laser shots deliverable by the probe. In such a scenario, the physician uses a fiber probe that is programmed to deliver 15 laser shots to treat glaucoma in a first eye of the subject. For sterilization purposes, a second fiber is programmed and used to deliver 15 laser shots in a second eye of the subject. The physician uses two fiber probes during the ELT procedure, one probe for each eye. In contrast, twice as many fiber probes would be used for the same ELT treatment plan if the physician was using traditional, fixed number fiber probes with 10 shots set as the maximum fixed number of shots. A first fixed number probe would be used to apply a maximum 10 shots to a first eye, the first fixed number probe would be replaced with a second fixed number probe, and the remaining 5 shots in the treatment plan would be applied to the first eye. The process would be repeated for treatment of a second eye of the subject, with a third fixed number probe used to apply a maximum 10 shots to the second eye and a fourth fixed number probe used to apply the remaining 5 shots in the treatment plan to the second eye.

In an embodiment of the invention, the input options on the interactive user interface are directed to setting the pulse, width, and amplitude of the laser. Due to safety concerns, a maximum setting for each of the pulse, width, and amplitude are typically pre-defined by the manufacturer. The user may select values within the predefined ranges set by the manufacturer.

Examples of the invention use a 308-nm xenon-chloride ultraviolet excimer laser. The 308-nm xenon-chloride ultraviolet excimer laser causes minimal thermal damage compared with visible or infrared lasers. In some examples of the invention, the excimer laser is an encapsulated xenon chloride (XeCl) excimer laser such as the EX TRA LASER manufactured by MLase AG. Because ELT is a non-thermal procedure, tissue reactions in the trabecular meshwork are not shown or activated post-operatively. The lack of heat generation in ELT allows for a nearly absent activation of postoperative tissue reactions and provides long-term stability of the pressure-reducing effects.

Moreover, to avoid the corneal absorption of laser radiation, an optical fiber is used to deliver the energy. A delivery tip of the fiber probe comprises the optical fiber jacketed in metal, such as stainless steel. In some examples of the invention, the delivery tip is beveled (e.g., at 0°, 15°, 30°, and 45° with respect to the tip). The fiber probe comprises an optical fiber suitable for UV light that is embedded into a handheld laser applicator. In some examples of the invention, a FIDO LASER APPLICATOR manufactured by MLase AG is used as the fiber probe.

DETAILED DESCRIPTION

Systems and methods of the invention treat glaucoma using excimer laser trabeculostomy (ELT). Multiple shots from the excimer laser are administered to the patient in order to shoot holes, or perforations, in the trabecular meshwork and/or Schlemm's canal. ELT converts trabecular meshwork tissue into gas by photoablation. By permanently perforating Schlemm's canal and/or the trabecular meshwork, built-up fluid in the eye is immediately allowed to drain. Moreover, because the perforations allow for increased blood flow and fluid drainage, subsequent vision loss from damage to the optic nerve due to any build-up is thereby avoided.

In existing fiber probes for use ELT procedures, the fiber probes are set to deliver a maximum fixed number of laser shots. Methods and systems of the present invention allow the physician to program the number of laser shots deliverable by the fiber probes, thereby providing fiber probes that deliverable a variable number of laser shots. Once the delivery tip is at a position transverse to the Schlemm's canal, the physician applies pulsed photoablative energy to create ELT sites or perforations in the trabecular meshwork and/or Schlemm's canal. In some examples of the invention, a physician creates greater than about 10 ELT sites per eye.

Figure 1:
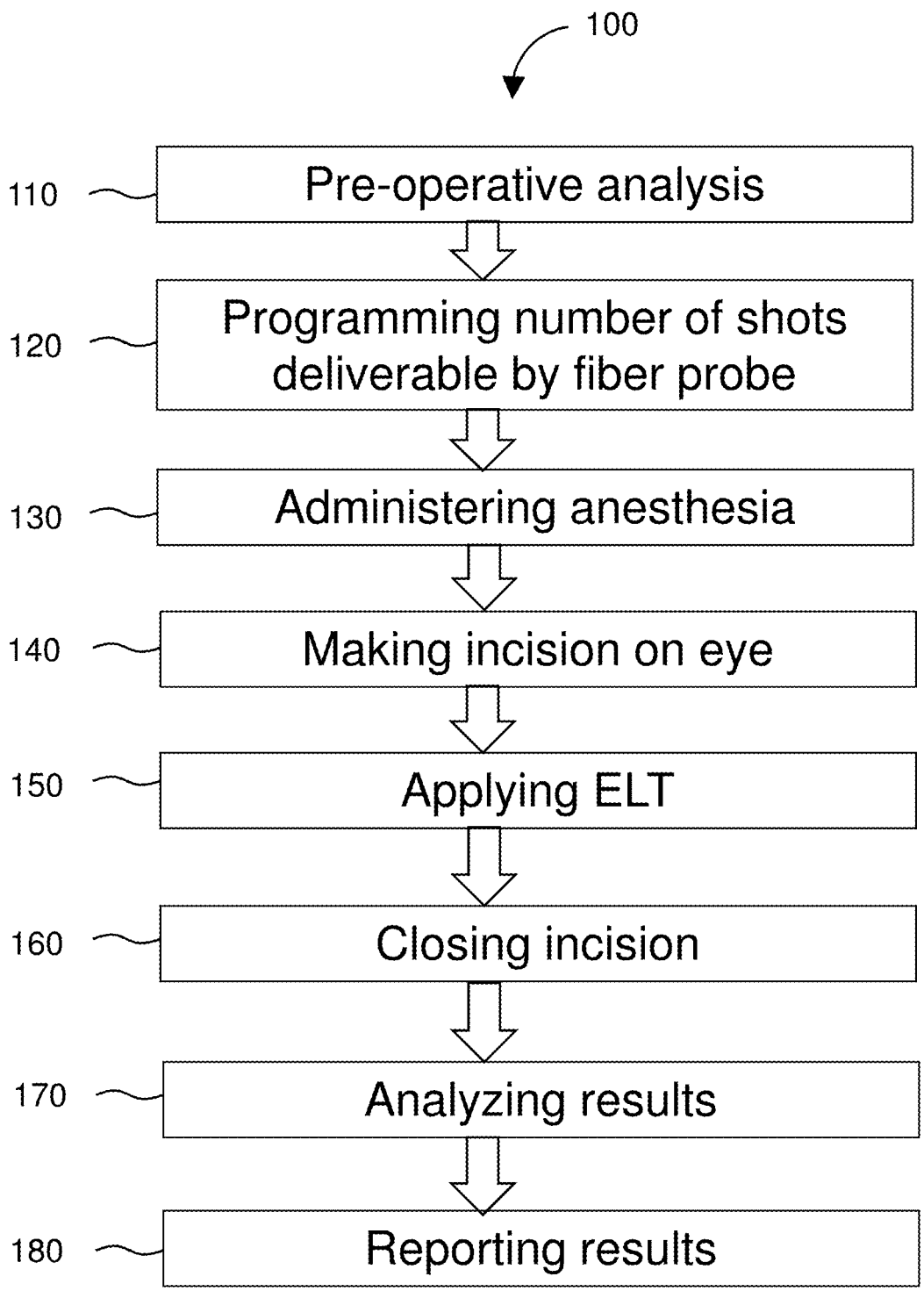
FIG. 1 is a flowchart of an embodiment of methods of the invention.

FIG. 1 shows a flowchart of an embodiment 100 of methods of the invention. Methods of the invention are directed to treating a patient having glaucoma with ELT. In the invention, the energy shots delivered from the excimer laser are at a position transverse to the Schlemm's canal. In some examples, methods include 110 pre-operative analysis, such as diagnosis of the eye condition, inspection and/or visualization of the anterior chamber of the eye to aid in placement of the laser probe, and analysis of number of laser shots needed for treatment. In the invention, excimer laser trabeculostomy (ELT) is used to treat glaucoma.

Methods of the invention include 120 programming the number of shots deliverable by the fiber probe. In existing fiber probes for use ELT procedures, the fiber probes are set to deliver a maximum, fixed number of laser shots. Methods and systems of the present invention allow the physician to program the number of laser shots deliverable by the fiber probes. The number of laser shots is programmable within a range and is adjustable from a minimum amount to a maximum amount. A physician can attach a fiber probe to the ELT instrument and use the interactive user interface on the instrument, and subsequently the controller and processor of the ELT system, to program the fiber probe to deliver a range of laser shots.

Some embodiments of the method include 130 administering anesthesia to the patient. Topical anesthesia is commonly employed, typically by the instillation of a local anesthetic such as tetracaine or lidocaine. Lidocaine and/or a longer-acting bupivacaine anesthetic may be injected into the area surrounding (peribulbar block) or behind (retrobulbar block) the eye muscle cone to more fully immobilize the extraocular muscles and minimize pain sensation. Optionally, a facial nerve block may be performed using lidocaine and bupivacaine to reduce lid squeezing. In some cases, such as for children, patients with traumatic eye injuries, and nervous or uncooperative patients and animals, general anesthesia is administered with cardiovascular monitoring. To prepare the area for surgery, proper sterile precautions must be taken, including use of antiseptics like povidone-iodine and employment of sterile drapes, gowns, and gloves. In some cases, an eye speculum is inserted to keep the eyelids open.

Methods of the invention further include a physician 140 making a small incision on the eye of the patient. Before the ELT procedure is performed, a small incision is made in the cornea of the eye to allow introduction of the laser probe. Typically, the incision is about ⅛ inch or smaller. During the ELT procedure, a physician guides a delivery tip of a fiber probe through the corneal incision in the eye and towards the trabecular meshwork. The delivery tip is guided by the physician to a position transverse to the Schlemm's canal. A Gonio lens, endoscope, and/or illumination source may be used by the physician to aid in positioning the delivery tip. By providing a laser probe at a position transverse to the Schlemm's canal, or crosswise to the Schlemm's canal, the laser is delivered to a greater amount of surface area than if the laser was in a parallel or perpendicular position to the Schlemm's canal. Thus, arrangement of the delivery tip at a position transverse to the Schlemm's canal achieves optimal photoablation and formation of perforations in the meshwork and/or Schlemm's canal. The orientation and positioning of the delivery tip is critical when creating perforations in the tissue, as achieving transverse placement of perforations in the meshwork relative to Schlemm's canal provides optimal drainage.

Once the delivery tip is at a position transverse to the Schlemm's canal, the physician 150 applies ELT treatment to the patient by delivering a series of shots of laser energy to the trabecular meshwork and Schlemm's canal. The physician applies pulsed photoablative energy to create ELT sites or perforations in the trabecular meshwork and/or Schlemm's canal. Unlike traditional fiber probes that have a maximum, fixed number of deliverable laser shots, methods of the invention allow the physician to program the number of shots deliverable by the fiber probe. The number of laser shots deliverable by fiber probes according to methods and systems of the invention is programmable within a range and is adjustable from a minimum amount to a maximum amount.

In some examples of the invention, a physician uses a programmed fiber probe to create greater than about 10 ELT sites in an eye of the patient. A small amount of bloody reflux from Schlemm's canal confirms each opening. The fiber probe is removed from the eye. Notably, the TOP decreases immediately after administering the ELT procedure.

After applying ELT treatment, a physician 160 closes the incision. Typically, a physician uses sutures to close the incision. Some physicians place a suture in the incision and other physicians reserve a suture for when there is persistent leakage.

Methods of the invention include 170 analyzing post-operative results and 180 reporting results and/or scheduling a post-operative follow-up appointment with the patient after surgery. For example, the physician's analysis may include observing a small amount of bloody reflux from Schlemm's canal to confirm each opening. By observing the bloody reflux and drainage of aqueous humor, the physician is able to immediately verify the effectiveness of the laser treatment. In turn, the physician may report the results to the patient, prescribe post-operative medication, such as topical antibiotics and steroid drops, and schedule a follow-up post-operative visit with the patient. For example, topical antibiotics and steroid drops are used by the patient for 1 to 2 weeks post-operatively.

Figure 2:
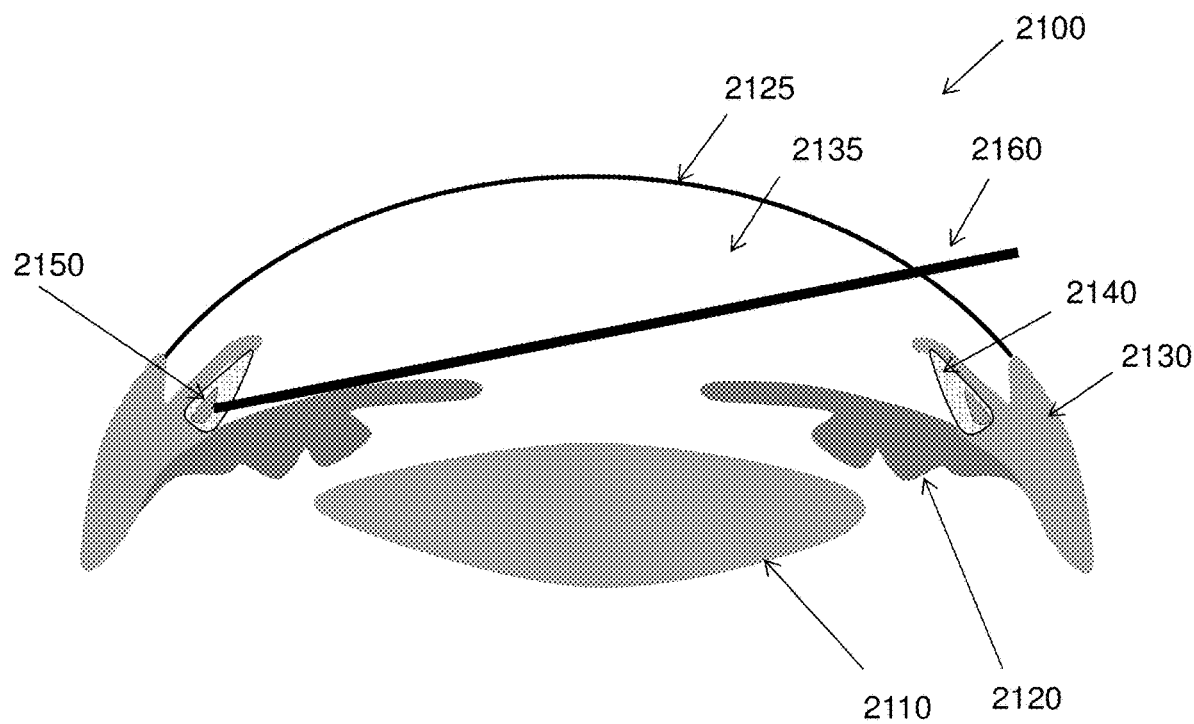
FIG. 2 is a schematic sectional view of an embodiment of the invention in an eye.
Figure 3:
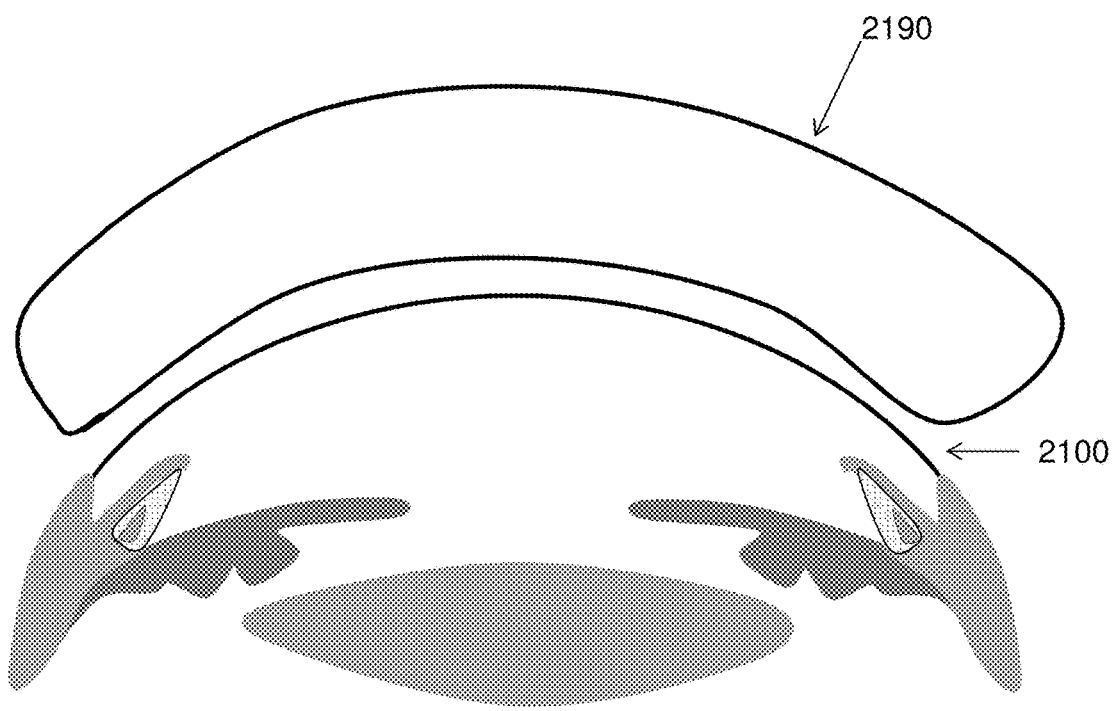
FIG. 3 shows the schematic section view of an eye with a light source aid.
Figure 4:
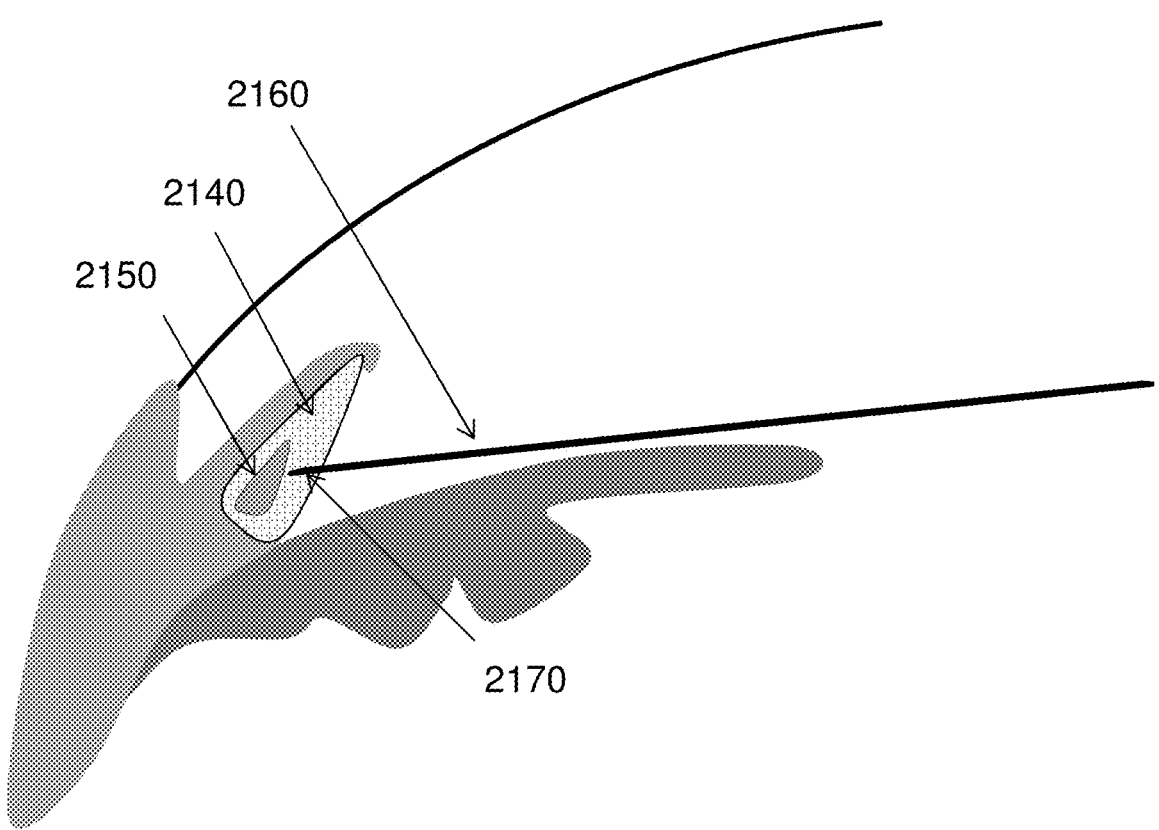
FIG. 4 is an enlarged schematic sectional view of an embodiment of the invention.

FIG. 2 is schematic sectional view of an eye 2100 illustrating the interior anatomical structure. FIG. 3 shows the schematic section view of an eye 2100 with a light source 2190, such as a Gonio lens, endoscope, or other light source. FIG. 4 is an enlarged schematic sectional view of the eye. The outer layer, or sclera, 2130 serves as a supporting framework for the eye, and the front of the outer layer 2130 includes a cornea 2125, a transparent tissue that enables light to enter the eye. An anterior chamber 2135 is located between the cornea 2125 and a crystalline lens 2110, and a posterior chamber is located behind the lens 2110. The anterior chamber 2135 contains a constantly flowing clear fluid called aqueous humor. In the anterior chamber 2135, an iris 2120 encircles the outer perimeter of the lens 2110 and includes a pupil at its center, which controls the amount of light passing through the lens 2110.

The eye further includes a trabecular meshwork 2140, which is a narrow band of spongy tissue that encircles the iris 2120 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 2140 has been measured to about a thickness of about 100 microns at its anterior edge, known as Schwalbe's line, which is at the approximate juncture of the cornea and sclera.

The trabecular meshwork widens to about 200 microns at its base where it and iris 2120 attach to the scleral spur. The passageways through the pores in trabecular meshwork 2140 lead through very thin, porous tissue called the juxtacanalicular trabecular meshwork that abuts the interior side of a structure called Schlemm's canal 2150. Schlemm's canal 2150 is filled with a mixture of aqueous humor and blood components and branches off into collector channels which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

The eye has a drainage system for the draining aqueous humor. The aqueous humor flows from a posterior chamber behind the lens 2110 through the pupil into the anterior chamber 2135 to the trabecular meshwork 2140 and into Schlemm's canal 2150 to collector channels and then to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork located between the trabecular meshwork 2140 and Schlemm's canal 2150, more specifically, the inner wall of Schlemm's canal. When an obstruction develops, such as at the juxtacanalicular trabecular meshwork or at Schlemm's canal, intraocular pressure gradually increases over time, leading to damage and atrophy of the optic nerve, subsequent visual field disturbances, and eventual blindness if left untreated.

A laser probe according to the invention is used to treat glaucoma. The delivery tip of the laser probe 2160 is guided through a small incision, typically about ⅛ inch or smaller, in the cornea 2125 of the eye and across the anterior chamber 2135 to a position transverse to the Schlemm's canal 2150. The laser probe is coupled to a laser source and transmits laser energy from the laser source to the trabecular meshwork 2140 and Schlemm's canal 2150, resulting in photoablation of tissue including at least the trabecular meshwork 2140 and, in some instances, the Schlemm's canal 2150. The photoablation from the laser energy creates perforations in the meshwork and/or Schlemm's canal, thereby improving fluid drainage into the Schlemm's canal 2150 and reducing intraocular pressure in the eye.

FIG. 4 shows the arrangement of the delivery tip 2160 at a position transverse 2170 to the Schlemm's canal 2150. Arrangement of the laser at a transverse position to the Schlemm's canal allows the laser path to travel crosswise through the trabecular meshwork to the Schlemm's canal. By positioning the laser transverse to the Schlemm's canal, the laser is able to provide photoablation to a greater amount of surface area of the trabecular meshwork in comparison to a laser arranged at positions perpendicular or parallel to the Schlemm's canal. Moreover, if the delivery tip of the laser was positioned parallel to the Schlemm's canal, the laser would not provide photoablation to any surface area of the trabecular meshwork or Schlemm's canal.

Figure 5:
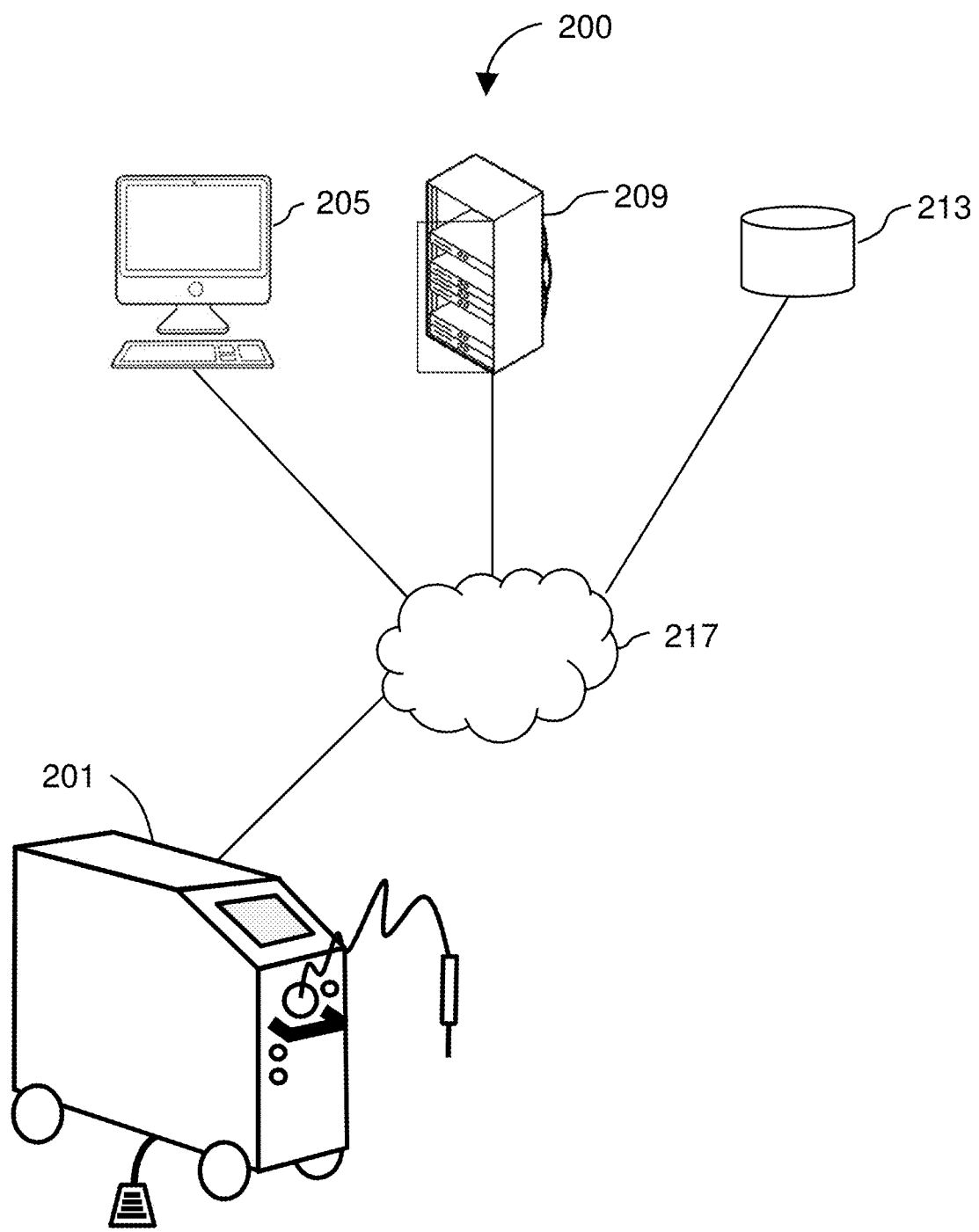
FIG. 5 shows an embodiment of systems of the invention.

FIG. 5 diagrams a schematic of system 200 according to certain embodiments of the invention. The system 200 includes an ELT instrument 201 communicatively coupled to a computer 205. The system 200 optionally includes a server 209 and storage 213. Any of the ELT instrument 201, the computer 205, the server 209, and the storage 213 that are included preferably exchange data via communication network 217. Where methods of the invention employ a client/server architecture, steps of methods of the invention may be performed using the server, which includes one or more of processors and memory, capable of obtaining data, instructions, etc., or providing results via an interface module or providing results as a file. The server may be provided by a single or multiple computer devices, such as the rack-mounted computers sold under the trademark BLADE by Hitachi. In system 200, each computer preferably includes at least one processor coupled to a memory and at least one input/output (I/O) mechanism.

A processor generally includes a chip, such as a single core or multi-core chip, to provide a central processing unit (CPU). A processor may be provided by a chip from Intel or AMD. Memory can include one or more machine-readable devices on which is stored one or more sets of instructions (e.g., software) which, when executed by the processor(s) of any one of the disclosed computers can accomplish some or all of the methodologies or functions described herein. A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. The system 200 may be used to perform methods described herein. Instructions for any method step may be stored in memory and a processor may execute those instructions.

Figure 6:
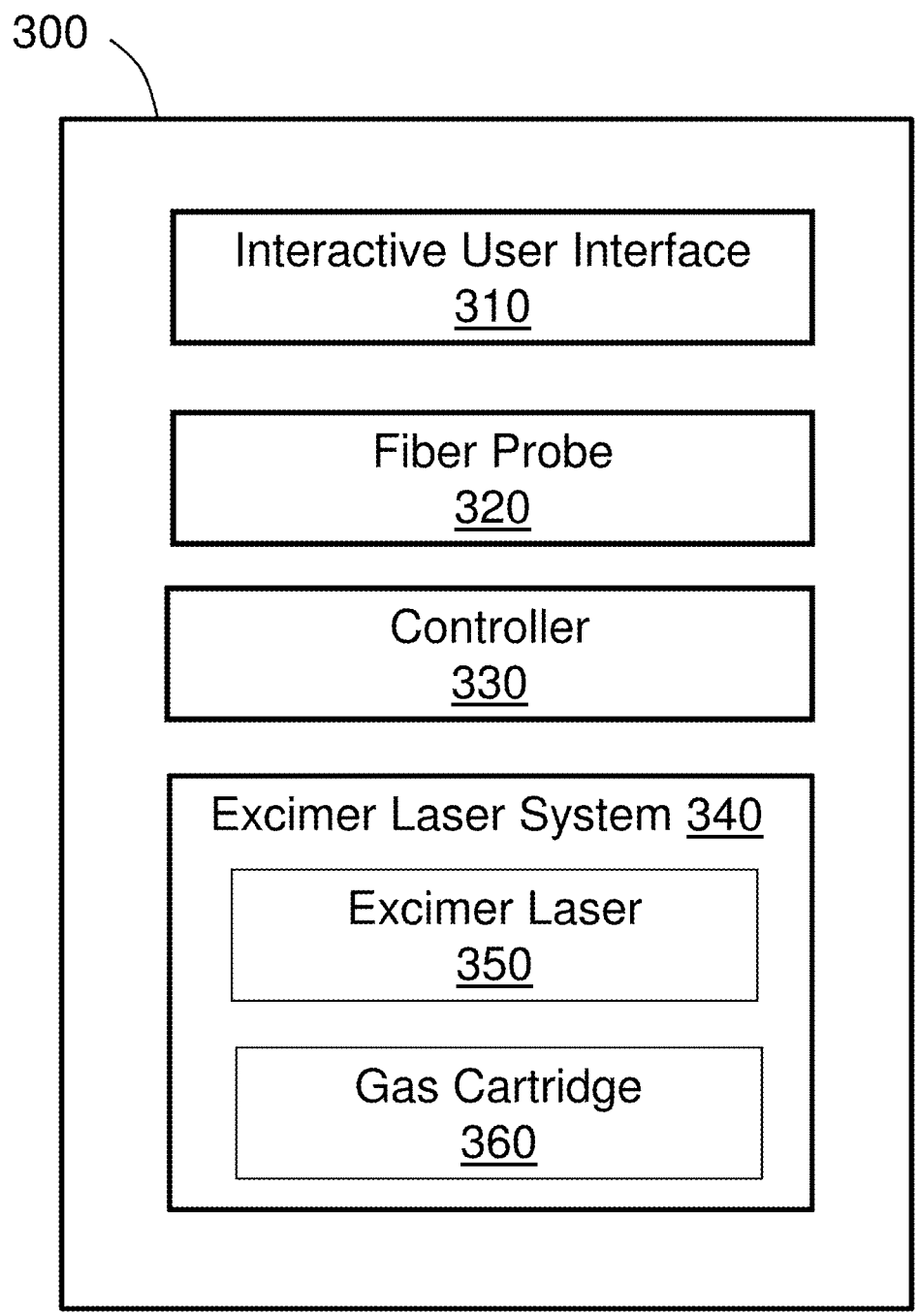
FIG. 6 shows an embodiment of systems of the invention.
Figure 9:
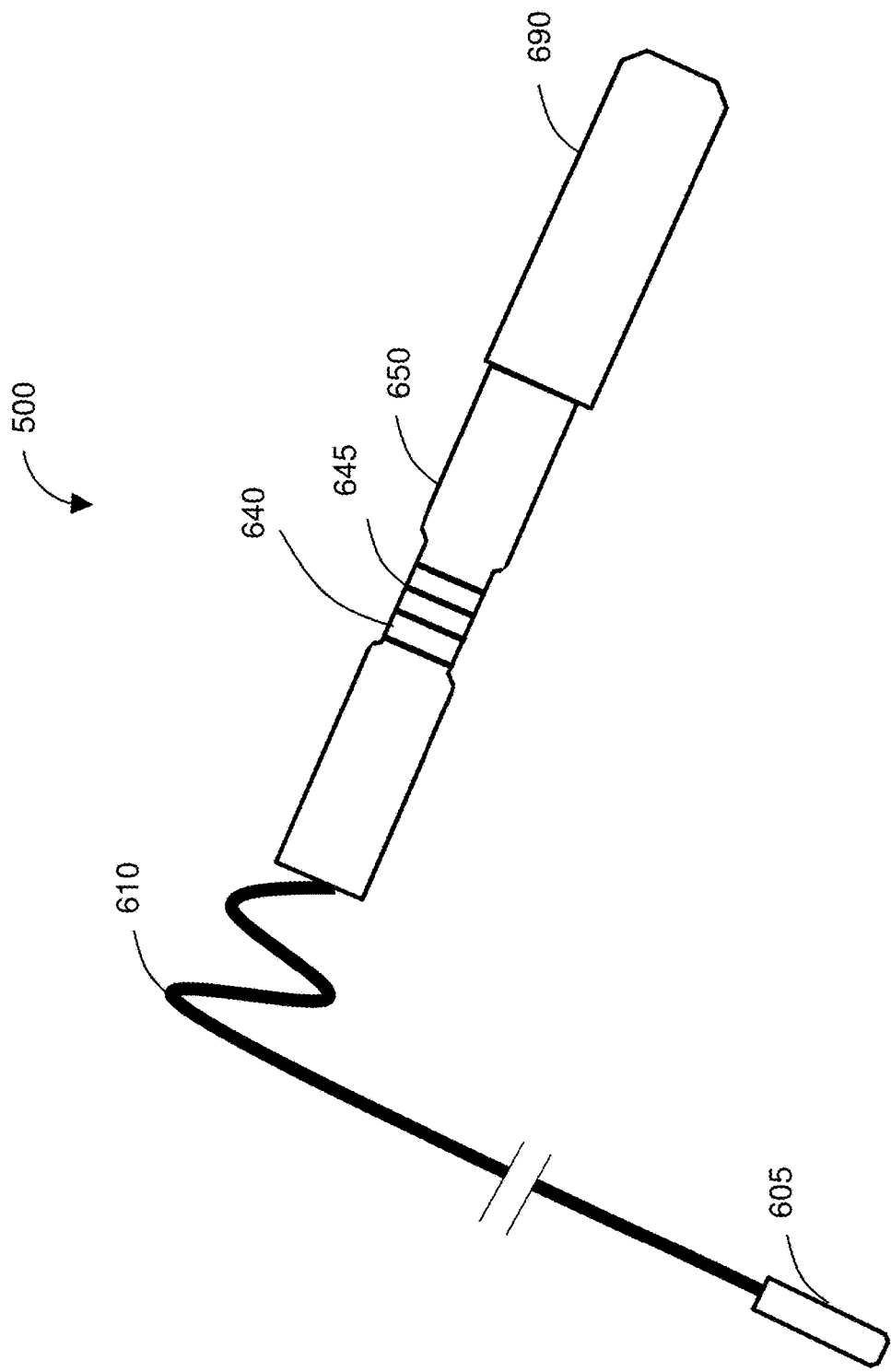
FIG. 9 shows a capped embodiment of a fiber probe.
Figure 10:
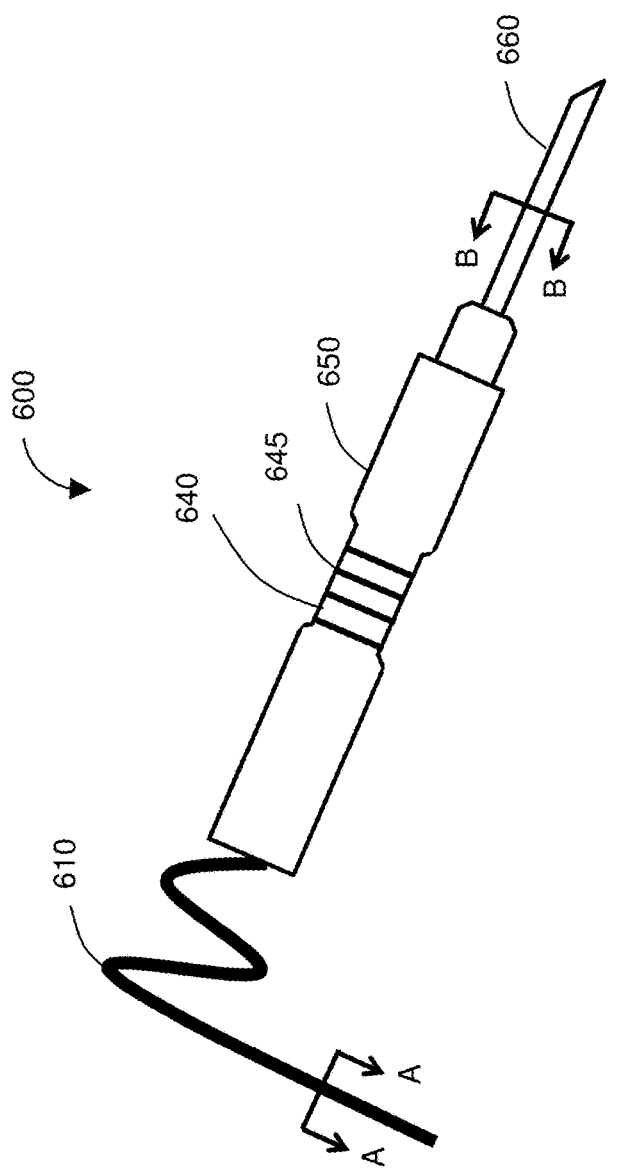
FIG. 10 shows an embodiment of a fiber probe.

FIG. 6 is a diagram of a system 300 for treating glaucoma according to the invention. The treatment system 300 comprises an interactive user interface 310 (example user interface 410 shown in FIG. 8), a fiber probe 320 (examples of fiber probes 500, 600 are shown in FIGS. 9 and 10), controller 330, and an excimer laser trabeculostomy (ELT) system 340 (example ELT device 400 shown in FIG. 7). The excimer laser system 340 comprises an excimer laser 350 and gas cartridge 360. The excimer laser system 340, interactive user interface 310, and fiber probe 320 are communicatively coupled to the controller 330. Moreover, the excimer laser system 340 may be contained in a housing that includes an interactive user interface, and a fiber probe may connect to the housing for use during ELT treatment.

The controller 330 has a processor. The processor generally includes a chip, such as a single core or multi-core chip, to provide a central processing unit (CPU), such as a chip from Intel or AMD. The controller 330 provides an operator (i.e., physician, surgeon, or other medical professional) with control over the treatment system 300, including programming of the fiber probe, output of laser signals, and control over the transmission of laser energy from the laser source 350 to the fiber probe 320 that delivers the laser transmission.

The controller 330 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 330 may include a hardware processor coupled to non-transitory, computer-readable memory containing instructions executable by the processor to cause the controller to carry out various functions of the treatment system 300 as described herein, including controlling the laser delivery and using the interactive user interface 310 to program the number of laser shots deliverable by the fiber probe 320.

The laser system 340 includes an excimer laser 350 and a gas cartridge 360 for providing the appropriate gas combination to the laser 350. The excimer laser 350 is a form of ultraviolet laser that generally operates in the UV spectral region and generates nanosecond pulses. The excimer gain medium (i.e., the medium contained within the gas cartridge 360) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 350 of the present system 300 is an XeCl excimer laser that emits a wavelength of 308 nm.

Figure 7:
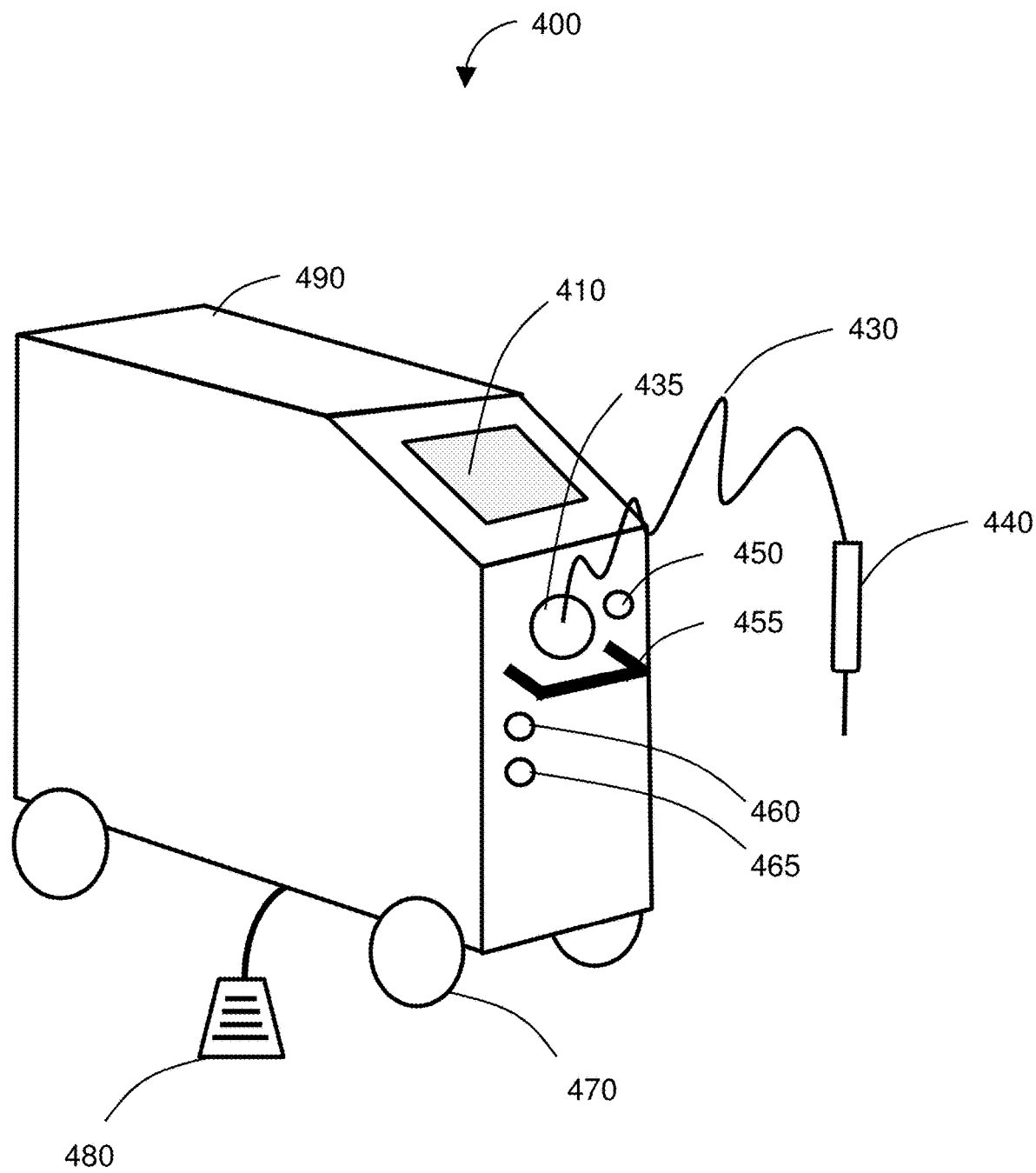
FIG. 7 shows an embodiment of an ELT system.

FIG. 7 shows an embodiment of the excimer laser trabeculostomy (ELT) instrument 400. An excimer laser is contained in the housing 490. The housing has wheels 470 and is portable. The push-pull handle 455 assists with portability of the ELT instrument 400. A foot pedal 480 extends from the housing 490 and is operable to provide power for delivering shots from the laser through the fiber probe 440. The connector 430 of the fiber probe 440 connects to the excimer laser in the housing 490 at the fiber connection port 435. The housing comprises an interactive user interface 410. In some examples, the interactive user interface 410 displays patient information, machine settings, and procedure information. The housing 490 includes control buttons, switches, and dials, such as a fiber probe cap holder 450, an emergency stop button 460, and a power switch 465.

Figure 8:
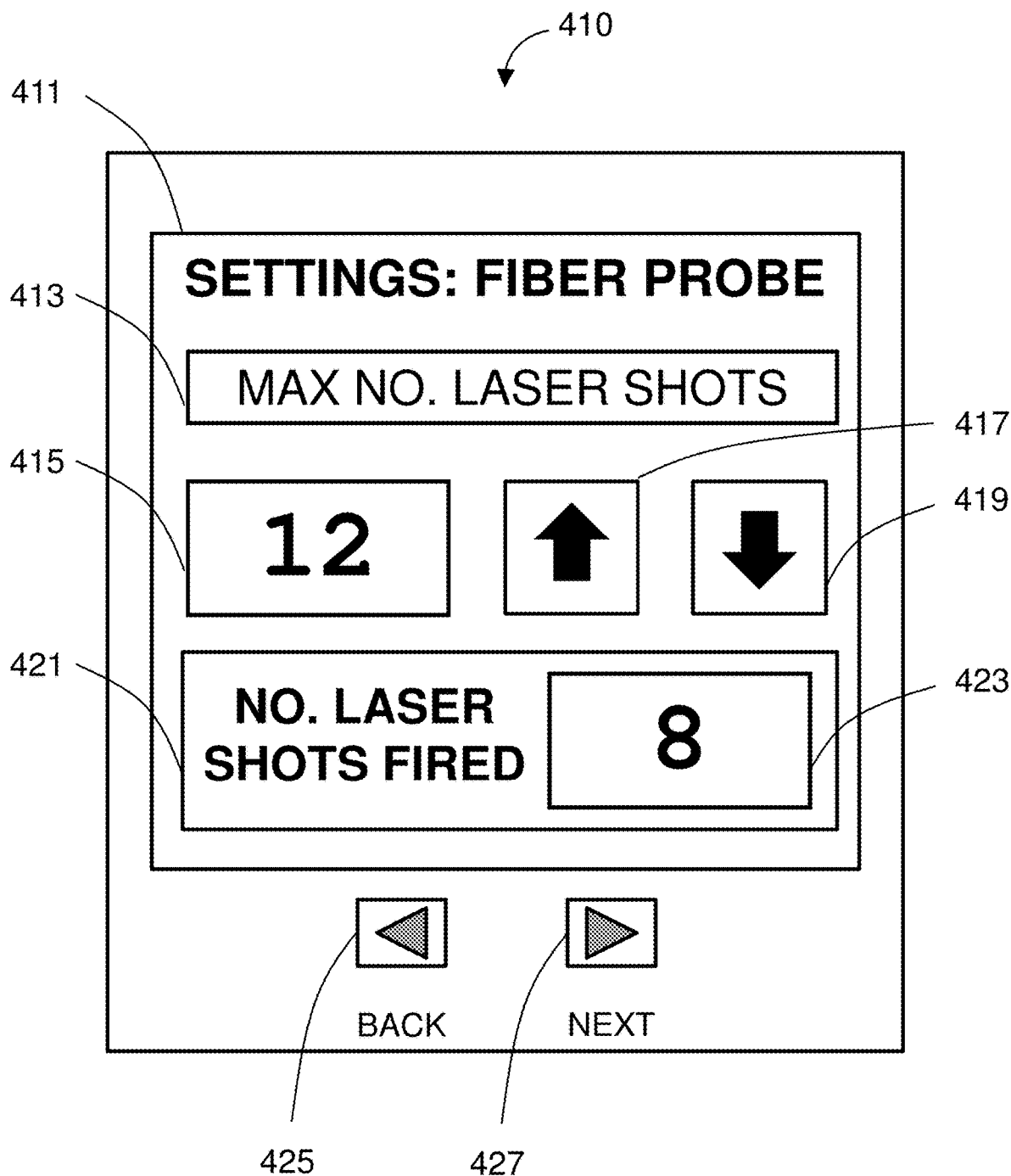
FIG. 8 shows a stylized embodiment of an interactive user interface.

FIG. 8 shows a stylized embodiment of an interactive user interface 410 according to the invention. The interactive user interface 410 is an interactive display screen on the ELT instrument. The interactive user interface 410 is communicatively coupled with the controller, which allows the user (e.g., physician) to view and change settings using the interactive user interface 410, such as via haptic feedback and/or touchscreen technologies. The interactive user interface displays a variety of information and settings, such as patient information, instrument information, and instrument settings.

Different information is displayed on a plurality of interchangeable display screens. For example, one screen may display setting information for the fiber probe, such as shown in FIG. 8, while another screen displays patient information. The user can view different screens by using button 425 to return to a previous screen or using button 427 to move forward to a next screen. In the embodiment shown in FIG. 8, a settings screen 411 is shown for the fiber probe. Display box 413 designates the setting, which is the maximum number of laser shots for the fiber probe. Display box 415 shows the maximum number of laser shots that the user has input. To change the set maximum number of laser shots, the user can select button 417 to increase the number in box 415 and button 419 to decrease the number in box 415. Display box 421 indicates the number of laser shots that have been fired from the probe, with the changing number shown in box 423. The embodiment shown in FIG. 8 indicates that the fiber probe has been programmed to deliver 12 shots as the maximum number of laser shots, and so far, the fiber probe has delivered 8 laser shots.

In an embodiment of the invention, the input options on the display screen are directed to setting the pulse, width, and amplitude of the laser. Due to safety concerns, a maximum setting for each of the pulse, width, and amplitude may be pre-defined by the manufacturer. The user may select values within the predefined ranges set by the manufacturer.

FIG. 9 shows a capped version of the fiber probe 500. FIG. 10 shows an uncapped version of the ELT probe or fiber probe 600. The fiber probe 500, 600 comprises an optical fiber 630 that runs through the fiber probe 600 and connects the fiber probe 600 to the excimer laser. The connector 610 comprises the optical fiber 630 surrounded by a protective sheath 620. In an example, the connector 610 is about 200 cm to about 300 cm in length. A proximal end of the connector has a connection plug 605 that is operable to interact with the connection point on the instrument. In an example of the invention, the connection plug 605 has threads that match up with threads on the connection port to secure the connector 610 to the instrument. In an example of the invention, the connection plug 605 has a ridge around the plug that matches up with a slot in the connection port to secure the connector 610 to the instrument. The connector 610 connects a connection point on the instrument (such as connection port 435 shown in FIG. 7) to the body 650 of the handheld fiber probe 600.

The fiber probe 600 is sterilized by any suitable method that provides sterilized equipment suitable for use on humans. In some embodiments, the fiber probe 600 is disposable. In some embodiments, the fiber probe 600 has a tag that determines operability. In some examples of the invention, a radio frequency identification (RFID) tag must match an RFID on the instrument in order to operate. In an embodiment, the body 650 of the handheld probe is plastic. In an embodiment, the body 650 of the fiber probe 500, 600 is about 5 cm to about 10 cm in length. Preferably, the body 650 of the fiber probe is about 7 cm in length. Optionally, the body may have a finger grip 640 with ridges 645. The fiber tip 660 at the distal end of the probe comprises an optical fiber 630 jacketed in metal 670, such as stainless steel or titanium. The jacketed fiber at the distal end of the probe is inserted into the trabecular meshwork of the eye. A foot pedal is depressed to power the laser. When powered, the laser delivers a shot from the laser that travels through the optical fiber to the trabecular meshwork and Schlemm's canal.

Figure 12:
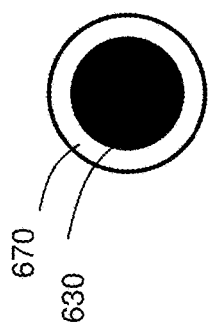
FIG. 12 shows a cross-sectional view of a fiber probe along line B-B of FIG. 10.
Figure 11:
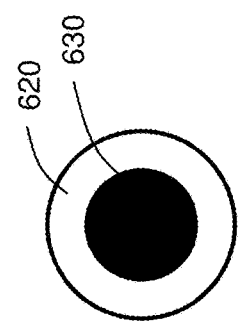
FIG. 11 shows a cross-sectional view of a fiber probe along line A-A of FIG. 10.

FIG. 11 shows a cross-sectional view of the fiber probe across line A-A of FIG. 10. The cross-section shown in A-A is the cross-section of the connector 610 from FIG. 10. A protective sheath 620 surrounds the optical fiber 630. In some examples, the protective sheath is a protective plastic or rubber sheath. FIG. 12 shows a cross-sectional view of the fiber probe across line B-B of FIG. 10. The cross-section shown in B-B is the cross-section of the fiber tip 660 from FIG. 10. A metal jacket 670 covers the optical fiber 630. In some cases, stainless steel jackets the optical fiber in the fiber tip.

INCORPORATION BY REFERENCE

References and citations to other documents, such as patents, patent applications, patent publications, journals, books, papers, and web contents made throughout this disclosure are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

The invention claimed is:

1. A system for treatment of glaucoma comprising:
   an excimer laser;
   a plurality of fiber probes, each fiber probe attachable to the excimer laser to treat a subject having glaucoma by delivering shots from the excimer laser, wherein each of the shots delivered from the excimer laser comprises pulses of photoablative energy;
   a display; and
   a processor configured to:
      receive a first signal from a user interface based on a first user input, wherein the first signal is indicative of a first user specified number of maximum shots deliverable by a first fiber probe of the plurality of fiber probes,
      cause the display to show the first user specified number of maximum shots,
      control the excimer laser to deliver no more than the first user specified number of maximum shots from the first fiber probe,
      monitor a first number of shots delivered by the first fiber probe,
      cause the display to show the first number of shots delivered by the first fiber probe,
      receive a second signal from the user interface based on a second user input, wherein the second signal is indicative of a second user specified number of maximum shots deliverable by a second fiber probe of the plurality of fiber probes, wherein the first user specified number is different from the second user specified number,
      cause the display to show the second user specified number of maximum shots, and
      control the excimer laser to deliver no more than the second user specified number of maximum shots from the second fiber probe.

2. The system of claim 1, wherein the first user specified number of maximum shots is a variable number programmable within a range from a minimum to a maximum.

3. The system of claim 2, wherein the first user specified number of maximum shots is greater than about 10 shots per eye.

4. The system of claim 1, wherein a delivery tip of the first fiber probe comprises an optical fiber jacketed in a metal.

5. The system of claim 4, wherein the metal is stainless steel.

6. The system of claim 4, wherein the delivery tip is beveled.

7. The system of claim 1, wherein the excimer laser is a xenon chloride laser.

8. The system of claim 1, wherein an interactive user interface is communicatively coupled to the processor for programming each of the plurality of fiber probes.

9. The system of claim 2, wherein the first user specified number of maximum shots is greater than 10 shots for at least one eye.

10. The system of claim 1, wherein each of the plurality of fiber probes comprises a tag that is indicative of operability.

11. The system of claim 10, wherein the tag comprises a radio frequency identification (RFID) tag.

12. The system of claim 1, wherein the processor is further configured to receive a third signal from the user interface based on a third user input, wherein the third signal is indicative of at least one of a pulse width or an amplitude of the laser.

13. The system of claim 1, wherein each of the plurality of fiber probes is associated with a predefined limit for a maximum number of shots deliverable.

14. The system of claim 13, wherein the first user specified number of maximum shots is set at or below a first predefined limit for the maximum number of shots deliverable for the first fiber probe, and wherein the second user specified number of maximum shots is set at or below a second predefined limit for the maximum number of shots deliverable for the second fiber probe.

15. The system of claim 1, wherein the first user specified number of maximum shots is selected from a predefined range of shots deliverable set by a manufacturer of the first fiber probe.

16. A system comprising:
   an excimer laser;
   a plurality of fiber probes attachable to the excimer laser and configured to deliver shots from the excimer laser, wherein each of the shots delivered from the excimer laser comprises pulses of photoablative energy;
   a display; and
   a processor configured to:
      monitor a first number of shots delivered by a first fiber probe of the plurality of fiber probes,
      cause the display to show the first number of shots delivered by the first fiber probe,
      monitor a second number of shots delivered by a second fiber probe of the plurality of fiber probes, wherein the first number of shots delivered is different from the second number of shots delivered, and
      cause the display to show the second number of shots delivered by the second fiber probe.

17. The system of claim 16, wherein the first number of shots delivered by the first probe is limited based on a specified number of maximum shots deliverable set by a manufacturer of the first fiber probe.

18. The system of claim 16, wherein the first fiber probe is associated with a predefined limit for a maximum number of shots deliverable.

19. A system comprising:
   an excimer laser;
   a plurality of fiber probes attachable to the excimer laser and configured to deliver shots from the excimer laser, wherein each of the plurality of fiber probes is further configured to deliver a variable number of shots programmable within a range from a minimum to a maximum, and further wherein each of the shots delivered from the excimer laser comprises pulses of photoablative energy;
   a display; and
   a processor configured to:
      receive a first signal from a user interface based on a first user input, wherein the first signal is indicative of a first user specified number of maximum shots deliverable by a first fiber probe of the at least one fiber probe,
      cause the display to show the first user specified number of maximum shots,
      control the excimer laser to deliver up to the first user specified number of maximum shots from the first fiber probe,
      receive a second signal from the user interface based on a second user input, wherein the second signal is indicative of a second user specified number of maximum shots deliverable by a second fiber probe of the at least one fiber probe, wherein the first user specified number is different from the second user specified number, cause the display to show the second user specified number of maximum shots, and control the excimer laser to deliver up to the second user specified number of maximum shots from the second fiber probe,.

20. The system of claim 19, wherein the user specified number of maximum shots is at least 12 shots.

* * * * *